United States Patent
Adams et al.

(10) Patent No.: US 6,548,520 B1
(45) Date of Patent: Apr. 15, 2003

(54) SUBSTITUTED IMIDAZOLES HAVING ANTI-CANCER AND CYTOKINE INHIBITORY ACTIVITY

(75) Inventors: Jerry L. Adams, Wayne, PA (US); Susan B. Dillon, Alamo, CA (US); Sandra D. Griego, Limerick, PA (US); Dennis Lee, San Mateo, CA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/701,460

(22) Filed: Mar. 3, 2001

Related U.S. Application Data

(60) Provisional application No. 60/086,449, filed on May 22, 1998.

(51) Int. Cl.[7] ................ A61K 31/4439; C07D 401/04
(52) U.S. Cl. ................ 514/341; 514/318; 514/255; 514/232.2; 514/314; 514/308; 546/194; 546/167; 546/148; 546/274.1; 544/364; 544/359; 544/124; 544/131
(58) Field of Search .............. 546/274.1, 194, 546/167, 148; 514/341, 318, 255, 232.2, 314, 308; 544/364, 359, 124, 131

(56) References Cited

U.S. PATENT DOCUMENTS

| | | | |
|---|---|---|---|
| 3,707,475 A | 12/1972 | Lombardino | 260/309 |
| 3,772,441 A | 11/1973 | Lombardino | 424/273 |
| 3,929,807 A | 12/1975 | Fitzi | 260/294.8 R |
| 3,940,486 A | 2/1976 | Fitzi | 424/263 |
| 4,058,614 A | 11/1977 | Baldwin | 424/263 |
| 4,199,592 A | 4/1980 | Cherkofsky | 424/273 |
| 4,348,404 A | 9/1982 | Whitney | 424/273 |
| 4,447,431 A | 5/1984 | Sallmann | 424/246 |
| 4,472,422 A | 9/1984 | Whitney | 424/273 |
| 4,503,065 A | 3/1985 | Wilkerson | 514/396 |
| 4,565,875 A | 1/1986 | Cavender | 548/336 |
| 4,686,231 A | 8/1987 | Bender et al. | 514/333 |
| 4,822,805 A | 4/1989 | Tasasugi et al. | 514/341 |
| 5,552,557 A | 9/1996 | Fujii | 548/337.1 |
| 5,593,991 A | 1/1997 | Adams et al. | 514/235.2 |
| 5,593,992 A | 1/1997 | Adams et al. | 514/235.8 |
| 5,620,999 A | 4/1997 | Weier et al. | 514/398 |
| 5,656,644 A | 8/1997 | Adams et al. | 514/341 |
| 5,658,903 A | 8/1997 | Adams et al. | 514/235.8 |
| 5,663,334 A | 9/1997 | Sheldrake et al. | 544/122 |
| 5,670,527 A | 9/1997 | Adams et al. | 514/341 |
| 5,686,455 A | 11/1997 | Adams et al. | 514/256 |
| 5,739,143 A | 4/1998 | Adams et al. | 514/275 |

FOREIGN PATENT DOCUMENTS

| | | | |
|---|---|---|---|
| WO | WO92/10190 | 6/1992 | |
| WO | WO92/10498 | 6/1992 | |
| WO | WO95/02591 | 1/1995 | |
| WO | WO96/21452 | 7/1996 | |
| WO | WO96/21654 | 7/1996 | |
| WO | WO96/40143 | 12/1996 | |
| WO | WO 97/12876 | 4/1997 | |
| WO | WO97/25046 | 7/1997 | |
| WO | WO97/25047 | 7/1997 | |
| WO | WO97/25048 | 7/1997 | |
| WO | WO97/33883 | 9/1997 | .......... A61K/31/44 |
| WO | WO97/35855 | 10/1997 | |
| WO | WO97/35856 | 10/1997 | |
| WO | WO 97/36587 | 10/1997 | |
| WO | WO 97/47618 | 12/1997 | |
| WO | WO98/22109 | 5/1998 | |
| WO | WO 98/47892 | 10/1998 | |
| WO | WO98/57966 | 12/1998 | .......... A61K/31/505 |
| WO | WO00/26209 | 5/2000 | |

OTHER PUBLICATIONS

CA 135:242227, Steadman et al. 2001.*
CA 135:19656, Dean et al., 2001.*
Dinarello et al., Rev.Infect.Diesease, 6, p.51 (1984).
Dinarello, J.Clin. Immun., 5(5), p.287–297 (1985).
R.P.Soni, Aust.J.Chem., 35, p.1493–6 (1982).
Poli et al., Proc.Nat'l Acad.Sci., 87, p.782–784 (1990).
VanLeusen et al., J.O.C., 42, p.1153 (1977).
Kumada et al., Tetrahedron Letters, 22, p.5319 (1981).
Pridgen, J.Org.Chem., 47, p.4319 (1982).
Stille, J.Amer.Chem.Soc., 109, p.5478 (1978).
Fischer et al., Rec.Trav.Chim.Pays.Bas., 84, p.439 (1965).
Sniekus, V., Tetrahedron Letters, 29, 2135 (1988).
Terashimia, M., Chem.Pharm.Bull., 11, p.4755 (1985).
Thompson, W.J., et al., J.Org.Chem., 49, p.5237 (1984).
Garigipati, R., Tetrahedron Letters, 31, p.190 (1989).
Engel & Steglich, liebigs Ann. Chem., 1916 (1978).
Strzybny et al., J. Org. Chem., 28, p.3381 (1963).
Zavyalov, et al., Khim Farm Zh, 26(3), p. 88 (1992) (With Translation).
Colotta et al., J. Immunol., 132(2), p.936 (1984).
Simon et al., J. Immunol. Methods, 84m p.85 (1985).
Becker et al., J. Immunol., 147, p.4307 (1991).
Gilbert, Synthesis, pp. 30–32 (1972).
Morton et al., Tetrahedron Letters, 4123 (1982).
Armarego, W. J. Chem. Soc., (JCSO49) p.561 (1962).
Kawasaki et al., J. Bio. Chem., 272(30), pp.18518–18521.
Uno, Bull. Chem. Soc. Japan., Vol. 69, pp. 1763–1767 (1996).
Katritzky, Synthesis, pp. 45–47 (1993).
Johnson, P.A., J.Chem.Soc., Perkin Trans., Vol. 1, pp.895–905 (1996).
Ishibashi, Chem. Pharm. Bull., 37(8), pp.2214–2216 (1989).

* cited by examiner

*Primary Examiner*—Jane Fan
(74) *Attorney, Agent, or Firm*—Dara L. Dinner; Stephen Venetianer; Charles M. Kinzig

(57) ABSTRACT

The present invention is related to novel 2-alkyl substituted imidazoles of formula (I) useful for the treatment of CSBP kinase mediated diseases.

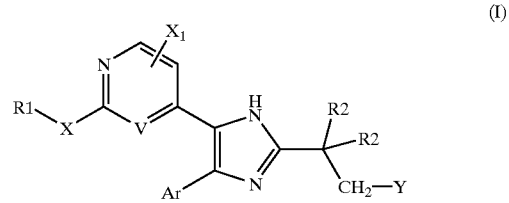

25 Claims, 2 Drawing Sheets

SUBSTITUTED IMIDAZOLES HAVING ANTI-CANCER AND CYTOKINE INHIBITORY ACTIVITY

This application is a 371 of PCT/US99/11260 May 20, 1999 now WO99/61437 which claim benefit of No. 60/086,449 May 22, 1998 under 35 USC 119(e).

FIELD OF THE INVENTION

This invention relates to a novel group of 2-position substituted imidazole compounds, processes for the preparation thereof, the use thereof in treating CSBP mediated diseases and pharmaceutical compositions for use in such therapy.

BACKGROUND OF THE INVENTION

Intracellular signal transduction is the means by which cells respond to extracellular stimuli. Regardless of the nature of the cell surface receptor (e.g. protein tyrosine kinase or seven-transmembrane G-protein coupled), protein kinases and phosphatases along with phopholipases are the essential machinery by which the signal is further transmitted within the cell [Marshall, J. C. Cell, 80, 179–278 (1995)]. Protein kinases can be categorized into five classes with the two major classes being, tyrosine kinases and serine/threonine kinases depending upon whether the enzyme phosphorylates its substrate(s) on specific tyrosine (s) or serine/threonine(s) residues [Hunter, T., Methods in Enzymology (Protein Kinase Classification) p. 3, Hunter, T.; Sefton, B. M.; eds. vol. 200, Academic Press; San Diego, 1991].

For most biological responses, multiple intracellular kinases are involved and an individual kinase can be involved in more than one signaling event. These kinases are often cytosolic and can translocate to the nucleus or the ribosomes where they can affect transcriptional and translational events, respectively. The involvement of kinases in transcriptional control is presently much better understood than their effect on translation as illustrated by the studies on growth factor induced signal transduction involving MAP/ERK kinase [Marshall, C. J. Cell, 80, 179 (1995); Herskowitz, I. Cell, 80, 187 (1995); Hunter, T. Cell, 80, 225 (1995);Seger, R., and Krebs, E. G. FASEB J., 726–735 (1995)].

While many signaling pathways are part of cell homeostasis, numerous cytokines (e.g., IL-1 and TNF) and certain other mediators of inflammation (e.g., COX-2, and iNOS) are produced only as a response to stress signals such as bacterial lippopolysaccharide (LPS). The first indications suggesting that the signal transduction pathway leading to LPS-induced cytokine biosynthesis involved protein kinases came from studies of Weinstein [Weinstein, et al., J. Immunol. 151, 3829(1993)] but the specific protein kinases involved were not identified. Working from a similar perspective, Han [Han, et al, Science 265, 808(1994)] identified murine p38 as a kinase which is tyrosine phosphorylated in response to LPS. Definitive proof of the involvement of the p38 kinase in LPS-stimulated signal transduction pathway leading to the initiation of proinflammatory cytokine biosynthesis was provided by the independent discovery of p38 kinase by Lee [Lee; et al., Nature, 372, 739(1994)] as the molecular target for a novel class of anti-inflammatory agents. The discovery of p38 (termed by Lee as CSBP 1 and 2) provided a mechanism of action of a class of anti-inflammatory compounds for which SK&F 86002 was the prototypic example. These compounds inhibited IL-1 and TNF synthesis in human monocytes at concentrations in the low uM range [Lee, et al., Int. J. Immunopharmac. 10(7), 835(1988)] and exhibited activity in animal models which are refractory to cyclooxygenase inhibitors [Lee; et al., Annals N. Y. Acad. Sci., 696, 149(1993)].

It is now firmly established that CSBP/p38 is a one of several kinases involved in a stress-response signal transduction pathway which is parallel to and largely independent of the analogous mitogen-activated protein kinase (MAP) kinase cascade (FIG. 1). Stress signals, including LPS, pro-inflammatory cytokines, oxidants, UV light and osmotic stress, activate kinases upstream from CSBP/p38 which in turn phosphorylate CSBP/p38 at threonine 180 and tyrosine 182 resulting in CSBP/p38 activation. MAPKAP kinase-2 and MAPKAP kinase-3 have been identified as downstream substrates of CSBP/p38 which in turn phosphorylate heat shock protein Hsp 27 (FIG. 2). It is not yet known whether MAPKAP-2, MAPKAP-3, Mnk1 or Mnk2 are involved in cytokine biosynthesis or alternatively that inhibitors of CSBP/p38 kinase might regulate cytokine biosynthesis by blocking a yet unidentified substrate downstream from CSBP/p38 [Cohen, P. Trends Cell Biol., 353–361(1997)].

What is known, however, is that in addition to inhibiting IL-1 and TNF, CSBP/p38 kinase inhibitors (SK&F 86002 and SB 203580) also decrease the synthesis of a wide variety of pro-inflammatory proteins including, IL-6, IL-8, GM-CSF and COX-2. Inhibitors of CSBP/p38 kinase have also been shown to suppress the TNF-induced expression of VCAM-1 on endothelial cells, the TNF-induced phosphorylation and activation of cytosolic PLA2 and the IL-1-stimulated synthesis of collagenase and stromelysin. These and additional data demonstrate that CSBP/p38 is involved not only cytokine synthesis, but also in cytokine signaling [CSBP/P38 kinase reviewed in Cohen, P. Trends Cell Biol., 353–361(1997)].

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al.. Rev. Infect. Disease, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis, and acute synovitis. Recent evidence also links IL-1 activity to diabetes and pancreatic β cells [review of the biological activities which have been attributed to IL-1 Dinarello, J. Clinical Imnnunology, 5 (5), 287–297 (1985)].

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, such as influenza, cachexia secondary to infection or malignancy, cachexia, secondary to acquired immune deficiency syndrome (AIDS), AIDS, ARC (ADS related complex), keloid formation, scar tissue formation, Crohn's disease, ulcerative colitis, or pyresis.

Interleukin-8 (IL-8) is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes, and basophils. In addition it induces histamine release from basophils from both normal and atopic individuals as well as lysozomal enzyme release and respiratory burst from neutrophils. IL-8 has also been shown to increase the surface expression of Mac-1 (CD11 b/CD18) on neutrophils without de novo protein synthesis, this may contribute to increased adhesion of the neutrophils to vascular endothelial cells. Many diseases are characterized by massive neutrophil infiltration. Conditions associated with an increased in IL-8 production (which is responsible for chemotaxis of neutrophil into the inflammatory site) would benefit by compounds which are suppressive of IL-8 production.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

Inhibition of signal transduction via CSBP/p38, which in addition to IL-1, TNF and IL-8 described above is also required for the synthesis and/or action of several additional pro-inflammatory proteins (i.e., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for CSBP/p38 kinase inhibitors [Badger, et al., *J. Pharm. Exp. Thera.* 279 (3): 1453–1461.(1996); Griswold, et al, *Pharmacol. Comm.* 7, 323–229 (1996)].

There remains a need for treatment, in this field, for compounds which are cytokine suppressive anti-inflammatory drugs, i.e. compounds which are capable of inhibiting the CSBP/p38/RK kinase.

SUMMARY OF THE INVENTION

Figure 1:
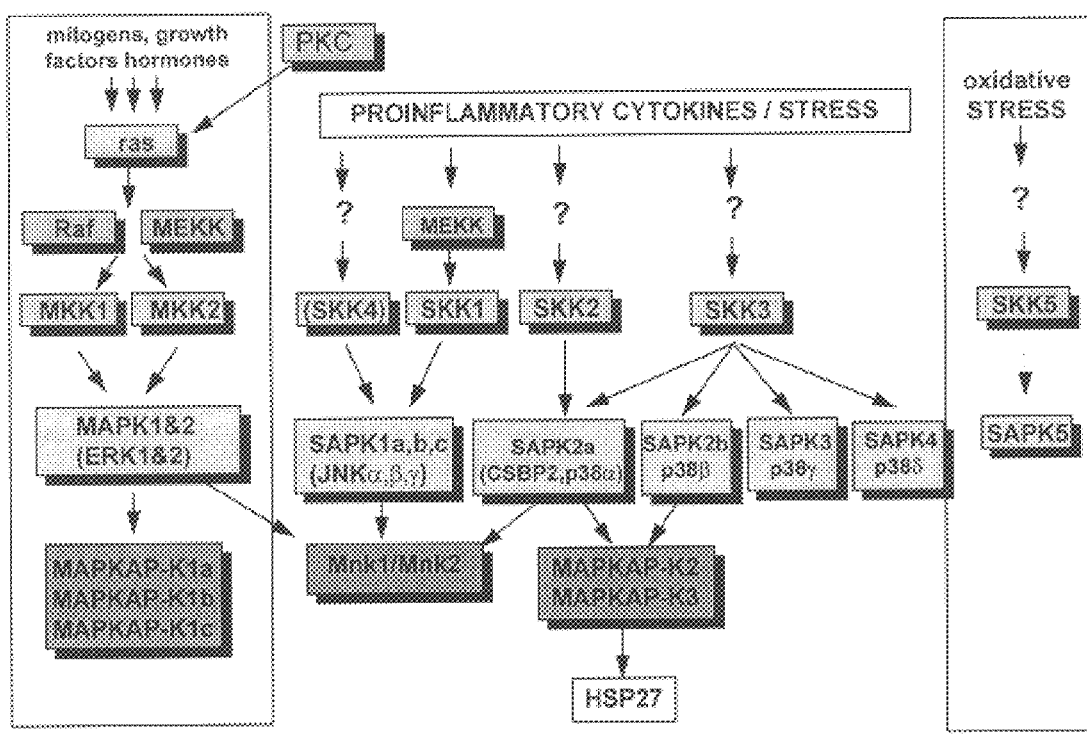
FIG. 1 demonstrates the mitogen-activated protein kinase (MAP) kinase cascade.
Figure 2:
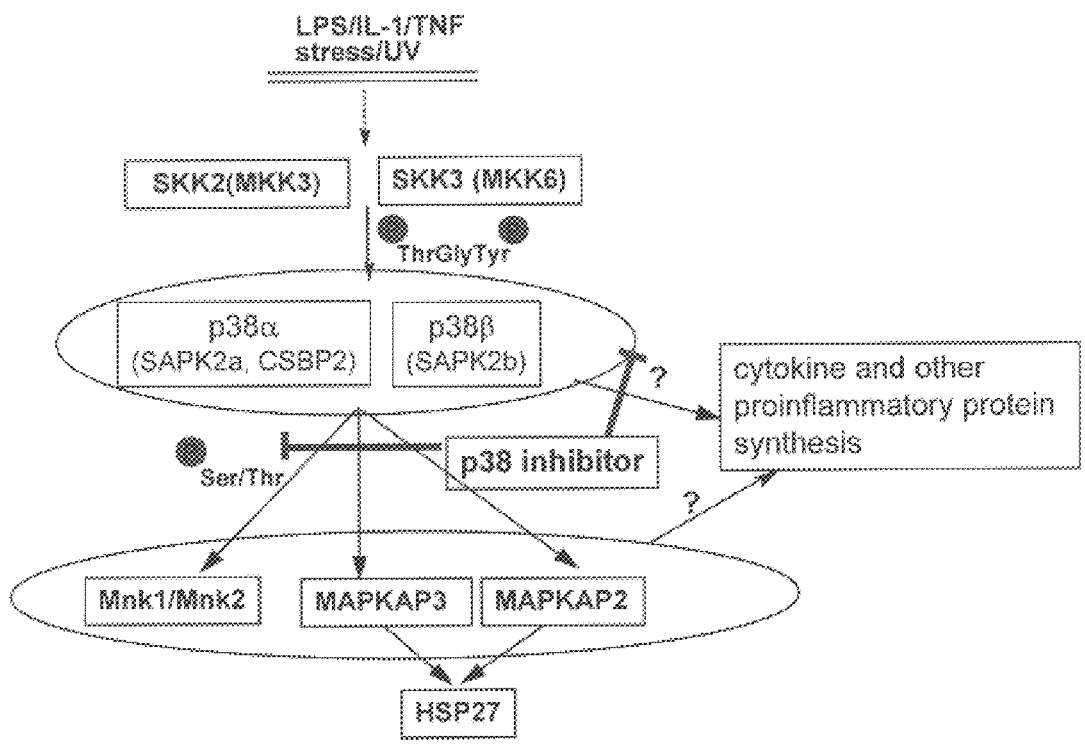
FIG. 2 demonstrates the p38 kinase pathway.

This invention relates to the novel compounds of Formula (I) and pharmaceutical compositions comprising a compound of Formula (I) and a pharmaceutically acceptable diluent or carrier.

This invention relates to a method of prophylaxis, or the treatment of a CSBP/RK/p38 kinase mediated disease in a mammal in need thereof, which method comprises administering to said mammal an effective prophylactic or treatment amount of a compound of Formula (I).

This invention also relates to a method of inhibiting cytokines and the treatment of a cytokine mediated disease, in a mammal in need thereof, which comprises administering to said mammal an effective amount of a compound of Formula (I).

Accordingly, the present invention provides for the novel compounds of Formula (I) represented by the structure:

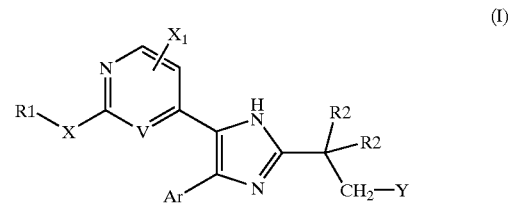

(I)

wherein
X is oxygen, carbon, sulfur, or nitrogen, or the moiety X—$R_1$ is hydrogen;

V is CH or N;

$R_1$ is hydrogen, $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl, wherein each of these moieties may be optionally substituted;

$X_1$ is hydrogen, $XR_1$, $NHR_a$, optionally substituted $C_{1-4}$ alkyl, halogen, hydroxyl, optionally substituted $C_{1-4}$ alkoxy, optionally substituted $C_{1-4}$ alkylthio, optionally substituted $C_{1-4}$ alkylsulfinyl, $CH_2OR_{12}$, amino, mono and di- $C_{1-6}$ alkyl substituted amino, $N(R_{10})C(O)R_b$, $N(R_{10})S(O)_2R_d$, or an N-heterocyclyl ring which ring has from 5 to 7 members and optionally contains an additional heteroatom selected from oxygen, sulfur or $NR_{15}$;

$R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl;

$R_d$ is $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl;

$R_2$ is independently an optionally substituted $C_{1-4}$ alkyl, and wherein the two $R_2$ moieties may together form a C3–7 cycloalkyl or C5–7 cycloalkenyl ring which ring may be optionally substituted;

Y is a $C_{2-4}$ alkenyl, hydroxy substituted $C_{1-4}$ alkyl, heterocyclic, C(Z)OH, or $N(R_{10})C(Z)R_3$;

$R_3$ is $C_{1-6}$alkyl, aryl, aryl$C_{1-6}$alkyl, heterocyclic, heterocyclyC$_{1-6}$ alkyl, heteroaryl, or heteroaryl$C_{1-6}$alkyl, wherein each of these moieties may be optionally substituted;

Ar is an aryl or heteroaryl ring which ring may be optionally substituted;

$R_{10}$ is hydrogen or $C_{1-4}$ alkyl;

$R_{12}$ is hydrogen, —$C(Z)R_{13}$ or optionally substituted $C_{1-4}$ alkyl, optionally substituted aryl, optionally substituted aryl$C_{1-4}$ alkyl, or $S(O)_2R_{25}$;

Z is oxygen or sulfur;

$R_{13}$ is hydrogen, $C_{1-10}$ alkyl, $C_{3-7}$ cycloalkyl, heterocyclyl, heterocyclyl$C_{1-10}$ alkyl, aryl, aryl$C_{1-10}$ alkyl, heteroaryl or heteroaryl $C_{1-10}$ alkyl, wherein all of these moieties may be optionally substituted;

$R_{15}$ is hydrogen, cyano, $C_{1-4}$ alkyl, $C_{3-7}$ cycloalkyl or aryl;

$R_{25}$ is $C_{1-10}$ alkyl, $C_{3-7}$ cycloalkyl, heterocyclyl, aryl, arylalkyl, heterocyclyl, heterocyclyl$C_{1-10}$alkyl, heteroaryl or heteroarylalkyl; or a pharmaceutically acceptable salt thereof.

FULL DESCRIPTION OF THE INVENTION

The novel compounds of Formula (I) may also be used in association with the veterinary treatment of mammals, other than humans, in need of inhibition of cytokine inhibition or production. In particular, cytokine mediated diseases for treatment, therapeutically or prophylactically, in animals include disease states such as those noted herein in the Methods of Treatment section, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

In compounds of Formula (I), suitably X is oxygen, carbon, sulfur or nitrogen or the moiety X—$R_1$ is hydrogen. Preferably X is oxygen, or nitrogen, more preferably oxygen.

Suitably $R_1$ is hydrogen, $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl, wherein each of these moieties may be optionally substituted. Preferably $R_1$ is $C_{1-6}$alkyl, aryl, or aryl$C_{1-6}$alkyl. When X is carbon, $R_1$ may be hydrogen, yielding a methyl group. When X is nitrogen, $R_1$ may be hydrogen, yielding an unsubstituted amino group.

Suitably when V is CH or N, the 5-position heteroring is a pyridine or pyridimine ring. This ring may be additionally substituted by $X_1$ wherein $X_1$ is hydrogen, $XR_1$, optionally substituted $C_{1-4}$ alkyl, halogen, hydroxyl, optionally substituted $C_{1-4}$ alkoxy, optionally substituted $C_{1-4}$ alkylthio, optionally substituted $C_{1-4}$ alkylsulfinyl, $CH_2OR_{12}$, amino, mono and di- $C_{1-6}$ alkyl substituted amino, $N(R_{10})C(O)R_b$, $N(R_{10})S(O)_2R_d$, or an N-heterocyclyl ring which ring has from 5 to 7 members and optionally contains an additional heteroatom selected from oxygen, sulfur or $NR_{15}$. Preferably $X_1$ is hydrogen. When $X_1$ is hydrogen, the X—$R_1$ moiety may also be hydrogen, yielding an unsubstituted pyrimidine or pyridyl ring.

Suitably, $R_{10}$ and are each independently selected from hydrogen or $C_{1-4}$ alkyl.

Suitably, $R_{12}$ is hydrogen, $C(Z)R_{13}$ or optionally substituted $C_{1-4}$ alkyl, optionally substituted aryl, optionally substituted aryl$C_{1-4}$ alkyl, or $S(O)_2R_{25}$.

Suitably, Z is oxygen or sulfur, preferably oxygen.

Suitably, $R_{13}$ is hydrogen, $C_{1-10}$ alkyl, $C_{3-7}$ cycloalkyl, heterocyclyl, heterocyclyl$C_{1-10}$ alkyl, aryl, aryl$C_{1-10}$ alkyl, heteroaryl or heteroaryl $C_{1-10}$ alkyl, wherein all of these moieties may be optionally substituted.

Suitably, $R_{25}$ is $C_{1-10}$ alkyl, $C_{3-7}$ cycloalkyl, heterocyclyl, aryl, arylalkyl, heterocyclyl, heterocyclyl-$C_{1-10}$alkyl, heteroaryl or heteroarylalkyl.

Suitably, $R_b$ is hydrogen, $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl; wherein each of these moieties may be optionally substituted.

Suitably, $R_d$ is $C_{1-6}$ alkyl, $C_{3-7}$ cycloalkyl, aryl, aryl$C_{1-4}$ alkyl, heteroaryl, heteroaryl$C_{1-4}$alkyl, heterocyclyl, or heterocyclyl$C_{1-4}$ alkyl; wherein each of these moieties may be optionally substituted.

Suitably, $R_2$ is independently an optionally substituted $C_{1-4}$ alkyl group, and the two $R_2$ moieties may together form a $C_{3-7}$ cycloalkyl or $C_{5-7}$ cycloalkenyl ring which ring may be optionally substituted.

Suitably, Y is a $C_{2-4}$ alkenyl, hydroxy substituted $C_{1-4}$ alkyl, heterocyclic ring, $C(Z)OH$, or $N(R_{10})C(Z)R_3$.

Suitably when Y is a heterocyclic ring, the ring may be optionally substituted one or more times as defined below. Preferably, the heterocyclic ring is a pyrrolidine, piperidine, piperazine, morpholine, imidazolidine or pyrazolidine ring.

Suitably, $R_3$ is $C_{1-6}$alkyl, aryl, aryl$C_{1-6}$alkyl, heterocyclic, heterocyclyl$C_{1-6}$ alkyl, heteroaryl, or heteroaryl$C_{1-6}$alkyl, wherein each of these moieties may be optionally substituted.

Suitably, Ar is an aryl or a heteroaryl ring which ring may be optionally substituted.

When Ar is an aryl moiety is is preferably a 4-phenyl, 4-naphth-1-yl or 5-naphth-2-yl moiety, and which is substituted independently by one to three substituents, which are halogen, $S(O)_mR_8$, $OR_8$, $(CR_{10}R_{20})_mNR_{10}R_{20}$, $NR_{10}C(Z)R_8$ or $NR_{10}S(O)_mR_{11}$.

Suitably, $R_8$ is hydrogen, heterocyclyl, heterocyclylalkyl or $R_{11}$.

Suitably, $R_{11}$ is $C_{1-10}$ alkyl, halo-substituted $C_{1-10}$ alkyl, $C_{2-10}$ alkenyl, $C_{2-10}$ alkynyl, $C_{3-7}$ cycloalkyl, $C_{5-7}$ cycloalkenyl, aryl, arylalkyl, heteroaryl or heteroarylalkyl.

Suitably, m is 0, or a number having the value of 1 or 2.

A preferred substituents for the 4-position in the aryl rings include halogen, especially fluoro and chloro, of which fluoro is especially preferred; and $SR_8$ and $SOR_8$ wherein $R_8$ is preferably a $C_{1-2}$ alkyl, more preferably methyl. Preferred 3-position substiutents in the aryl rings include: halogen, especially chloro; $OR_8$, especially $C_{1-4}$ alkoxy; amino; $NR_{10}C(Z)R_8$, especially $NHCO(C_{1-10}$ alkyl); and $NR_{10}S(O)_m R_{11}$, especially $NHSO_2(C_{1-10}$ alkyl). The Ar moiety is prefereably an unsubstituted or substituted phenyl moiety. When substituted the Ar is more preferably substituted at the 4-position with fluoro and/or substituted at the 3-position with fluoro, chloro, $C_{1-4}$ alkoxy, methanesulfonamido or acetamido.

When Ar is a heteroaryl, which includes but is not limited to pyrrole, quinoline, isoquinoline, pyridine, pyrimidine, oxazole, thiazole, thiadiazole, triazole, imidazole, or benzimidazole, or indolyl, the ring may be optionally substituted (in any ring) independently by one or more, preferably by one to three substituents, which are halogen, $S(O)_mR_8$, $OR_8$, $(CR_{10}R_{20})_mNR_{10}R_{20}$, $NR_{10}C(Z)R_8$ or $NR_{10}S(O)_mR_{11}$.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of formula (I) may also be formed with a pharmaceutically acceptable cation, for instance, if a substituent $Y_1$ in $R_3$ comprises a carboxy group. Suitable pharmaceutically acceptable cations are well known to those skilled in the art and include alkaline, alkaline earth, ammonium and quarternary ammonium cations.

The following terms, as used herein, refer to:

"halo"—all halogens, that is chloro, fluoro, bromo and iodo;

"C$_{1-10}$alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, and the like;

"cycloalkyl" is used herein to mean cyclic radicals, preferably of 3 to 8 carbons, including but not limited to cyclopropyl, cyclopentyl, cyclohexyl, and the like.

"cycloalkenyl" is used herein to mean cyclic radicals, preferably of 5 to 8 carbons, which have at least one bond including but not limited to cyclopentenyl, cyclohexenyl, and the like.

"aryl"—phenyl and naphthyl;

"heteroaryl" (on its own or in any combination, such as "heteroaryloxy")—a 5–10 membered aromatic ring system in which one or more rings contain one or more heteroatoms selected from the group consisting of N, O or S, such as, but not limited, to pyrrole, quinoline, isoquinoline, pyridine, pyrimidine, oxazole, thiazole, thiadiazole, triazole, imidazole, or benzimidazole;

"heterocyclic" (on its own or in any combination, such as "heterocyclylalkyl")—a saturated or wholly or partially unsaturated 4–10 membered ring system in which one or more rings contain one or more heteroatoms selected from the group consisting of N, O or S; such as, but not limited to, pyrrolidine, piperidine, piperazine, morpholine, imidazolidine or pyrazolidine;

"aroyl"—a C(O)Ar, wherein Ar is as phenyl, naphthyl, or aryl alkyl derivative such as defined above, such group include but are note limited to benzyl and phenethyl;

"alkanoyl"—a C(O)C$_{1-10}$alkyl wherein the alkyl is as defined above;

"sulfinyl"—the oxide S(O) of the corresponding sulfide, while the term "thio" refers to the sulfide;

"aralkyl" or "heteroarylalkyl" or "heterocyclicalkyl" is used herein to mean an aryl, heteroaryl or heterocyclic moiety as respectively defined above said group connected to C$_{1-6}$ alkyl group as also defined above unless otherwise indicated.

As used herein, "optionally substituted" unless specifically defined shall mean such groups as halogen, such as fluorine, chlorine, bromine or iodine; hydroxy; hydroxy substituted C$_{1-10}$alkyl; C$_{1-10}$ alkoxy, such as methoxy or ethoxy; halosubstituted C$_{1-10}$ alkoxy; S(O)m alkyl, wherein m is 0, 1, or 2, such as methyl thio, methylsulfinyl or methyl sulfonyl; NR$_7$R$_{17}$, such as a amino or mono or disubstituted C$_{1-4}$ alkyl or wherein the R$_7$R$_{17}$ can cyclize together with the nitrogen to which they are attached to form a 5 to 7 membered ring which optionally contains an additional heteroatom selected from O/N/S; C$_{1-10}$ alkyl, C$_{3-7}$cycloalkyl, or C$_{3-7}$cycloalkyl C$_{1-10}$ alkyl group, such as methyl, ethyl, propyl, isopropyl, t-butyl, etc. or cyclopropyl methyl; halosubstituted C$_{1-10}$ alkyl, such CF$_2$CF$_2$H, or CF$_3$; an optionally substituted aryl, such as phenyl, or an optionally substituted arylalkyl, such as benzyl or phenethyl, wherein these aryl moieties may also be substituted one to two times by halogen; hydroxy; hydroxy substituted alkyl; C$_{1-10}$ alkoxy; S(O)$_m$alkyl; amino, mono & di-substituted C$_{1-4}$ alkyl amino; C$_{1-4}$ alkyl, or CF$_3$.

Suitably, R$_7$ and R$_{17}$ are each independently selected from hydrogen or C$_{1-4}$ alkyl or R$_7$ and R$_{17}$ together with the nitrogen to which they are attached form a heterocyclic ring of 5 to 7 members which ring optionally contains an additional heteroatom selected from oxygen, sulfur or nitrogen.

It is recognized that the compounds of the present invention may exist as stereoisomers, regioisomers, or diastereiomers. These compounds may contain one or more asymmetric carbon atoms and may exist in racemic and optically active forms. All of these compounds are included within the scope of the present invention.

Compounds of Formula (I) are imidazole derivatives which may be readily prepared using procedures well-known to those skilled in the art, and described in, for instance, Comprehensive Heterocyclic Chemistry, Editors Katritzky and Rees, Pergamon Press, 1984, 5, 457–497, from starting materials which are either commercially available or can be prepared from such by analogy with well-known processes. A key step in many such syntheses is the formation of the central imidazole nucleus, to give compounds of formula (I). Suitable procedures are described in inter alia U.S. Pat. Nos. 3,707,475 and 3,940,486 which are herein incorporated by reference in their entirety. These patents describe the synthesis of a-diketones and a-hydroxyketones (benzoins) and their subsequent use in preparing imidazoles and N-hydroxyl imidazoles. Thereafter, further compounds of formula (I) may be obtained by manipulating substituents in any of the groups R$_1$, R$_2$, R$_3$ and R$_4$ using conventional functional group interconversion procedures.

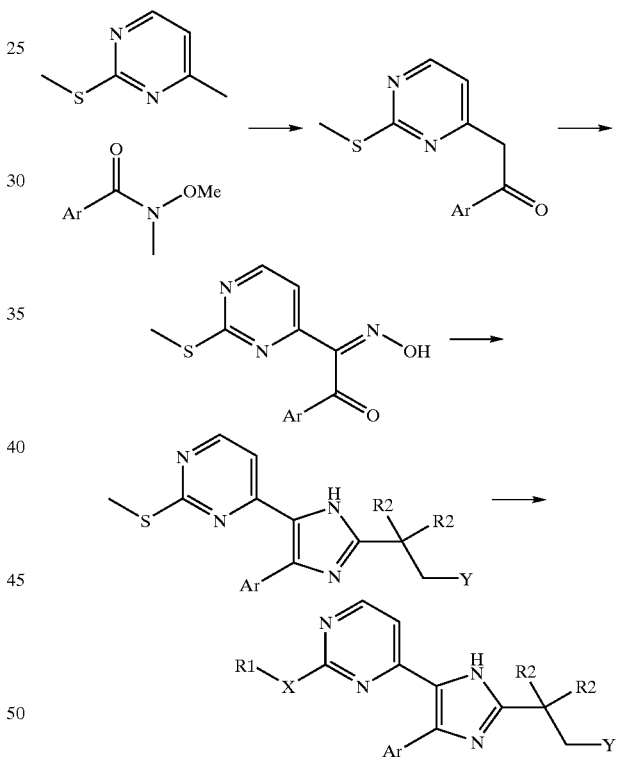

Compounds of the general formula (V=N, X=O, N, S) can be prepared as outlined in the above scheme. Condensation of the anion of 4-methyl-2-(methylthio)pyrimidine with the Weinreb amide of an aryl acid will yield the ketone, which upon oxidation with sodium nitrite affords the ketooxime. Heating this product with an alkyl aldehyde and ammonium acetate in acetic acid allows access to the imidazole nucleus. Replacement of the methylthio-group with nucleophiles (X=O,N,S) can be effected by oxidation to the methylsulfinyl derivative with 3-chloroperoxybenzoic acid or oxone, followed by displacement with nucleophiles with or without the addition of bases such as sodium hydride, organolithiums or trialkylamines. In the case of amines (X=N), aluminum amide derivatives can be used to effect the displacements.

Compounds of the general formula (V=CH, X=O, N, S) can be prepared as in Example 1 except substituting 4-methyl-2-chloropyridine for 4-methylpyridine (Gallagher el al Bioorg. Med Chem. 5, 49, 1997). Nucleophilic substitution of the resulting 2-chloropyridinylimidazole can be effected by the procedure described in U.S. Pat. No. 5,670,527.

Alternative synthesis for making compounds of Formula (I) are described in U.S. Ser. No. 08/481,671, Adams et al.; and in PCT/US93/00674, now U.S. Pat. No. 5,686,455, Adams et al., whose disclosures are incorporated by reference herein in their entirety.

Once the imidazole nucleus has been established, further compounds of formula (I) which may be prepared by applying standard techniques for functional group interconversion. For instance: —C(O)NR$_{13}$R$_{14}$ from —CO$_2$CH$_3$ by heating with or without catalytic metal cyanide, e.g. NaCN, and HNR$_{13}$R$_{14}$ in CH$_{30}$H; —OC(O)R$_3$ from —OH with e.g., ClC(O)R$_3$ in pyridine; —NR$_{10}$—C(S)NR$_{13}$R$_{14}$ from —NHR$_{10}$ with an alkylisothiocyante or thiocyanic acid; NR$_6$C(O)OR$_6$ from —NHR$_6$ with the alkyl chloroformate; —NR$_{10}$C(O)NR$_{13}$R$_{14}$ from —NHR$_{10}$ by treatment with an isocyanate, e.g. HN=C=O or R$_{10}$N=C=O; —NR$_{10}$—C(O)R$_8$ from —NHR$_{10}$ by treatment with Cl—C(O)R$_3$ in pyridine; —C(=NR$_{10}$)NR$_{13}$R$_{14}$ from —C(NR$_{13}$R$_{14}$)SR$_3$ with H$_3$NR$_3$$^+$OAc$^-$ by heating in alcohol; —C(NR$_{13}$R$_{14}$)SR$_3$ from —C(S)NR$_{13}$R$_{14}$ with R$_6$-I in an inert solvent, e.g. acetone; —C(S)NR$_{13}$R$_{14}$ (where R$_{13}$ or R$_{14}$ is not hydrogen) from —C(S)NH$_2$ with HNR$_{13}$R$_{14}$—C(=NCN)—NR$_{13}$R$_{14}$ from —C(=NR$_{13}$R$_{14}$)—SR$_3$ with NH$_2$CN by heating in anhydrous alcohol, alternatively from —C(=NH)—NR$_{13}$R$_{14}$ by treatment with BrCN and NaOEt in EtOH; —NR$_{10}$—C(=NCN)SR$_8$ from —NHR$_{10}$ by treatment with (R$_8$S)$_2$C=NCN; —NR$_{10}$SO$_2$R$_3$ from —NHR$_{10}$ by treatment with ClSO$_2$R$_3$ by heating in pyridine; —NR$_{10}$C(S)R$_3$ from —NR$_{10}$C(O)R$_8$ by treatment with Lawesson's reagent [2,4-bis(4-methoxyphenyl)-1,3,2,4-dithiadiphosphetane-2,4-disulfide]; —NR$_{10}$SO$_2$CF$_3$ from —NHR$_6$ with triflic anhydride and base and wherein R$_3$, R$_6$, R$_{10}$, R$_{13}$ and R$_{14}$ are as defined below or as is described in U.S. Pat. No. 5,593,991 whose disclosure is incorporated herein by reference in its entirety.

Wherein R$_3$ is heterocyclyl, heterocyclylC$_{1-10}$ alkyl or R$_8$.

Wherein R$_6$ is hydrogen, a pharmaceutically acceptable cation, C$_{1-10}$ alkyl, C$_{3-7}$ cycloalkyl, aryl, arylC$_{1-4}$ alkyl, heteroaryl, heteroarylalkyl, heterocyclyl, aroyl, or C$_{1-10}$ alkanoyl.

Wherein R$_8$ is C$_{1-10}$ alkyl, halo-substituted C$_{1-10}$ alkyl, C$_{2-10}$ alkenyl, C$_{2-10}$ alkynyl, C$_{3-7}$ cycloalkyl, C$_{5-7}$ cycloalkenyl, aryl, arylC$_{1-10}$ alkyl, heteroaryl, heteroaryC$_{1-10}$ alkyl, (CR$_{10}$R$_{20}$)$_n$OR$_{11}$, (CR$_{10}$R$_{20}$)$_n$S(O)$_m$R$_{18}$, (CR$_{10}$R$_{20}$)$_n$NHS(O)$_2$R$_{18}$, (CR$_{10}$R$_{20}$)$_n$NR$_{13}$R$_{14}$; wherein the aryl, arylalkyl, heteroaryl, heteroaryl alkyl may be optionally substituted. Suitably, n is an integer having a value of 1 to 10.

Wherein R$_{10}$ and R$_{20}$ is each independently selected from hydrogen or C$_{1-4}$ alkyl.

Wherein R$_{13}$ and R$_{14}$ is each independently selected from hydrogen or optionally substituted C$_{1-4}$ alkyl, optionally substituted aryl or optionally substituted aryl-C$_{1-4}$ alkyl, or together with the nitrogen which they are attached form a heterocyclic ring of 5 to 7 members which ring optionally contains an additional heteroatom selected from oxygen, sulfur or nitrogen.

Suitable protecting groups for use with hydroxyl groups and the imidazole nitrogen are well known in the art and described in many references, for instance, Protecting Groups in Organic Synthesis, Greene T W, Wiley-Interscience, New York, 1981. Suitable examples of hydroxyl protecting groups include silyl ethers, such as t-butyldimethyl or t-butyldiphenyl, and alkyl ethers, such as methyl connected by an alkyl chain of variable link, (CR$_{10}$R$_{20}$)n. Suitable examples of imidazole nitrogen protecting groups include tetrahydropyranyl.

It should be noted that the compounds of Formula (I), where Ar is substituted by an alkylsulfinyl, arylsulfinyl, alkylsulfonyl, or arylsulfonyl group are prodrugs which are reductively converted in vivo to the corresponding alkylthio or arylthio form.

Pharmaceutically acid addition salts of compounds of formula (I) may be obtained in known manner, for example by treatment thereof with an appropriate amount of acid in the presence of a suitable solvent.

The invention will now be described by reference to the following examples which are merely illustrative and are not to be construed as a limitation of the scope of the present invention.

SYNTHETIC EXAMPLES

Example 1

Specific examples for compounds of the general formula (V=CH, RIX=H) are prepared and shown below:

2-(1,1-dimethyl-3-butenyl)-4-(4-fluorophenyl)-5-(4-pyridinyl)imidazole

To [(2'-(t-Butyl-dimethylsilyloxy))-2'-(4-pyridyl)]aceto-(4-fluorophenone) (573 mg, 1.66 mmol) (prepared by the procedure of Gallagher et al (Bioorg. Med. Chem. 5, 49, 1997) in acetic acid (8 mL) was added 2,2-dimethyl-4-pentenal (271 uL, 1.99 mmol), ammonium acetate (716 mg, 9.3 mmol) and copper (II) acetate (329 mg, 1.8 mmol) at RT. The mixture was heated to 80° for 18 h. The solution was poured into ice, basified with ammonium hydroxide, and extracted with ethyl acetate. The organic extract was washed with saturated brine, dried (MgSO$_4$) and concentrated in vacuo. The residue was purified by flash chromatography (silica gel, 1–2% methanol/methylene chloride) to yield the title compound (123 mg). MS(ES$^+$) m/e 322 [M+H]$^+$.

Example 2

2-[2-(N-Benzoyl-N-methylamino)-(1,1-dimethyl)ethyl]-4-(4-fluorophenyl)-5-(4-pyridinyl)imidazole Following the procedure of Example 1, except substituting 3-(N-Benzoyl-N-methylamino)-2,2-dimethylpropenal for 2,2-dimethyl-4-pentenal, the title compound was prepared. MS(ES$^+$) m/e 429 [M+H]$^+$.

Example 3

(+/−)-2-[(3,4-Dihydroxy)-1,1-dimethylbutyl]-4-(4-fluorophenyl)-5-(4-pyridinyl)imidazole To a solution of the title compound of Example 1 (13.5 mg, 48 umol) in 8:1 acetone:water (0.5 mL) was added 4-methylmorpholine-N-oxide (6.7 mg, 57 umol) and a drop of osmium tetroxide (2.5% in 2-methyl-2-propanol). The solution was stirred at Room temperature (RT) overnight, and concentrated in vacuo. The residue was purified by flash chromatography (silica gel, 5–9% methanol/methylene chloride) to yield the title compound (10 mg). MS(ES$^+$) m/e 356 [M+H]$^+$.

Example 4

2-[(2-(2-Carboxy-1,1-dimethylethyl]-4-(4-fluorophenyl)-5-(4-pyridinyl)imidazole

To a solution of the title compound of Example 1 (52 mg, 186 umol) in 2:2:3 carbon tetrachloride:acetonitrile:water (1.3 mL) was added sodium periodate (163 mg, 762 umol) and catalytic ruthenium trichloride (2 mg). The solution was stirred at RT overnight. Water (5 mL) was added and the mixture was extracted with methylene chloride. The organic extract was dried (MgSO4), concentrated in vacuo, and the residue was purified by flash chromatography (silica gel, 2% methanol/methylene chloride followed by 0.1% acetic acid in 2–5% methanol/methylene chloride) to yield the title compound (4 mg). MS(ES$^+$) m/e 340 [M+H]$^+$.

Methods of Treatment

The compounds of Formula (I) or a pharmaceutically acceptable salt thereof can be used in the manufacutre of a medicament for the prophylactic or therapeutic treatment of any disease state in a human, or other mammal, which is exacerbated or caused by excessive or unregulated cytokine producution by such mammal's cell, such as but not limited to monocytes and/or macrophages.

Compounds of formula (I) are capable of inhibiting proinflammatory cytokines, such as IL-1, IL-6, IL-8 and TNF and are therefore of use in therapy. IL-1, IL-6, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Compounds of Formula (I) are capable of inhibiting inducible proinflammatory proteins, such as COX-2, also referred to by many other names such as prostaglandin endoperoxide synthase-2 (PGHS-2) and are therefore of use in therapy. These proinflammatory lipid mediators of the cyclooxygenase (CO) pathway are produced by the inducible COX-2 enzyme. Regulation, therefore of COX-2 which is responsible for the these products derived from arachidonic acid, such as prostaglandins affect a wide variety of cells and tissues are important and critical inflammatory mediators of a wide variety of disease states and conditions. Expression of COX-1 is not effected by compounds of Formula (I). This selective inhibition of COX-2 may alleviate or spare ulcerogenic liability associated with inhibition of COX-1 thereby inhibiting prostoglandins essential for cytoprotective effects. Thus inhibition of these pro-inflammatory mediators is of benefit in controlling, reducing and alleviating many of these disease states. Most notably these inflammatory mediators, in particular prostaglandins, have been implicated in pain, such as in the sensitization of pain receptors, or edema. This aspect of pain management therefore includes treatment of neuromuscular pain, headache, cancer pain, and arthritis pain. Compounds of Formula (I) or a pharmaceutically acceptable salt thereof, are of use in the prophylaxis or therapy in a human, or other mammal, by inhibition of the synthesis of the COX-2 enzyme.

Accordingly, the present invention provides a method of inhibiting the synthesis of COX-2 which comprises administering an effective amount of a compound of Formula (I) or a pharmaceutically acceptable salt thereof. The present invention also provides for a method of prophylaxis treatment in a human, or other mammal, by inhibition of the synthesis of the COX-2 enzyme.

Accordingly, the present invention provides a method of treating a cytokine-mediated disease which comprises administering an effective cytokine-interferring amount of a compound of formula (I) or a pharmaceutically acceptable salt thereof.

In particular, compounds of formula (I) or a pharmaceutically acceptable salt thereof are of use in the prophylaxis or therapy of any disease state in a human, or other mammal, which is exacerbated by or caused by excessive or unregulated IL-1, IL-6, IL-8 or TNF production by such mammal's cell, such as, but not limited to, monocytes and/or macrophages.

Accordingly, in another aspect, this invention relates to a method of inhibiting the production of IL-1 in a mammal in need thereof which comprises administering to said mammal an effective amount of a compound of formula (I) or a pharmaceutically acceptable salt thereof.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, rheumatoid arthritis, gout, traumatic arthritis, rubella arthritis and acute synovitis. Recent evidence also links IL-1 activity to diabetes, pancreatic β cells and Alzheimer's disease.

In a further aspect, this invention relates to a method of inhibiting the production of TNF in a mammal in need thereof which comprises administering to said mammal an effective amount of a compound of formula (I) or a pharmaceutically acceptable salt thereof.

Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, such as osteoporosis, reperfusion injury, graft vs. host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid formation, scar tissue formation, Crohn's disease, ulcerative colitis and pyresis.

Compounds of formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds of formula (1). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal, preferably a human, afflicted with a human immunodeficiency virus (HIV) which comprises administering to such mammal an effective TNF inhibiting amount of a compound of formula (I) or a pharmaceutically acceptable salt thereof.

It is also recognized that both IL-6 and IL-8 are produced during rhinovirus (HRV) infections and contribute to the pathogenesis of common cold and exacerbation of asthma associated with HRV infection (Turner et al. (1998), Clin. Infec. Dis., Vol 26, p 840; Teren et al. (1997), Am J Respir Crit Care Med vol 155, p1362; Grunberg et al. (1997), Am J Respir Crit Care Med 156:609 and Zhu et al, J Clin Invest (1996), 97:421). It has also been demonstrated in vitro that infection of pulmonary epithelial cells with HRV results in production of IL-6 and IL-8 (Subauste et al., J. Clin. Invest. 1995, 96:549.) Epithelial cells represent the primary site of infection of HRV. Therefore another aspect of the present invention is a method of treatment to reduce inflammation associated with a rhinovirus infection, not necessarily a direct effect on virus itself.

Compounds of formula (I) may also be used in association with the veterinary treatment of mammals, other than in humans, in need of inhibition of TNF production. TNF mediated diseases for treatment, therapeutically or prophylactically, in animals include disease states such as those noted above, but in particular viral infections. Examples of such viruses include, but are not limited to, the lentivirus infections such as equine infectious anaemia virus, caprine arthritis virus, visna virus, or the maedi virus, or the retroviruses, such as feline immunodeficiency virus (FIV), bovine immunodeficiency virus, or canine immunodeficiency virus.

The compounds of formula (I) may also be used topically in the treatment or prophylaxis of topical disease states mediated by or exacerbated by excessive cytokine production, such as by IL-1 or TNF respectively, such as inflamed joints, eczema, psoriasis and other inflammatory skin conditions such as sunburn; inflammatory eye conditions including conjunctivitis; pyresis, pain and other conditions associated with inflammation.

Compounds of formula (I) have also been shown to inhibit the production of IL-8 (Interleukin-8, NAP). Accordingly, in a further aspect, this invention relates to a method of inhibiting the production of IL-8 in a mammal in need thereof which comprises administering to said mammal an effective amount of a compound of formula (I) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac and renal reperfusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutophil infiltration.

The compounds of formula (I) are administered in an amount sufficient to inhibit cytokine, in particular IL-1, IL-8 or TNF, production such that it is regulated down to normal levels, or in some case to subnormal levels, so as to ameliorate or prevent the disease state. Abnormal levels of IL-1, IL-8 or TNF, for instance in the context of the present invention, constitute: (i) levels of free (not cell bound) IL-1, IL-8 or TNF greater than or equal to 1 picogram per ml; (ii) any cell associated IL-1, IL-8 or TNF; or (iii) the presence of IL-1, IL-8 or TNF mRNA above basal levels in cells or tissues in which IL-1, IL-8 or TNF, respectively, is produced.

The discovery that the compounds of formula (I) are inhibitors of cytokines, specifically IL-1, IL-8 and TNF is based upon the effects of the compounds of formulas (I) on the production of the IL-1, IL-8 and TNF in in vitro assays which are described herein.

As used herein, the term "inhibiting the production of IL-1 (IL-8 or TNF)" refers to:

a) a decrease of excessive in vivo levels of the cytokine (IL-1, IL-8 or TNF) in a human to normal or sub-normal levels by inhibition of the in vivo release of the cytokine by all cells, including but not limited to monocytes or macrophages;

b) a down regulation, at the genomic level, of excessive in vivo levels of the cytokine (IL-1, IL-8 or TNF) in a human to normal or sub-normal levels;

c) a down regulation, by inhibition of the direct synthesis of the cytokine (IL-1, L-8 or TNF) as a postranslational event; or d) a down regulation, at the translational level, of excessive in vivo levels of the cytokine (IL-1, IL-8 or TNF) in a human to normal or sub-normal levels.

As used herein, the term "TNF mediated disease or disease state" refers to any and all disease states in which TNF plays a role, either by production of TNF itself, or by TNT causing another monokine to be released, such as but not limited to IL-1, IL-6 or IL-8. A disease state in which, for instance, IL-1 is a major component, and whose production or action, is exacerbated or secreted in response to TNF, would therefore be considered a disease stated mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphoctye cells. Examples of cytokines include, but are not limited to, Interleukin-1 (IL-1), Interleukin-6 (IL-6), Interleukin-8 (IL-8), Tumor Necrosis Factor-alpha (TNF-a) and Tumor Necrosis Factor beta (TNF-$\beta$).

As used herein, the term "cytokine interfering" or "cytokine suppresive amount" refers to an effective amount of a compound of formula (I) which will cause a decrease in the in vivo levels of the cytokine to normal or sub-normal levels, when given to a patient for the prophylaxis or treatment of a disease state which is exacerbated by, or caused by, excessive or unregulated cytokine production.

As used herein, the cytokine referred to in the phrase "inhibition of a cytokine, for use in the treatment of a HIV-infected human" is a cytokine which is implicated in (a) the initiation and/or maintenance of T cell activation and/or activated T cell-mediated HV gene expression and/or replication and/or (b) any cytokine-mediated disease associated problem such as cachexia or muscle degeneration.

As TNF-$\beta$ (also known as lymphotoxin) has close structural homology with TNF-a (also known as cachectin) and since each induces similar biologic responses and binds to the same cellular receptor, both TNF-a and TNF-$\beta$ are inhibited by the compounds of the present invention and thus are herein referred to collectively as "TNF" unless specifically delineated otherwise.

A new member of the MAP kinase family, alternatively termed CSBP, p38, or RK, has been identified independently by several laboratories recently [See Lee et al., Nature, Vol. 300 n(72), 739–746 (1994)]. Activation of this novel protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors, of the present invention, compounds of Formula (I), have been determined to be potent and selective inhibitors of CSBP/p38/RK kinase activity. These inhibitors are of aid in determining the signaling pathways involvement in inflammatory responses. In particular, for the first time a definitive signal transduction pathway can be prescribed to the action of lipopolysaccharide in cytokine production in macrophages. In addition to those diseases already noted, treatment of stroke, neurotrauma, cardiac and renal reperfusion injury, thrombosis, glomerulonephritis, diabetes and pancreatic β cells, multiple sclerosis, muscle degeneration, eczema, psoriasis, sunburn, and conjunctivitis are also included.

The cytokine inhibitors were subsequently tested in a number of animal models for anti-inflammatory activity. Model systems were chosen that were relatively insensitive to cyclooxygenase inhibitors in order to reveal the unique activities of cytokine suppressive agents. The inhibitors exhibited significant activity in many such in vivo studies. Most notable are its effectiveness in the collagen-induced arthritis model and inhibition of TNF production in the endotoxic shock model. In the latter study, the reduction in plasma level of TNF correlated with survival and protection from endotoxic shock related mortality. Also of great importance are the compounds effectiveness in inhibiting bone resorption in a rat fetal long bone organ culture system. Griswold et al., (1988) *Arthritis Rheum.* 31:1406–1412; Badger, et al., (1989) *Circ. Shock* 27, 51–61; Votta et al., (1994)in vitro. *Bone* 15, 533–538; Lee et al., (1993). B *Ann. N. Y. Acad. Sci.* 696, 149–170.

In order to use a compound of formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of formula (I) and a pharmaceutically acceptable carrier or diluent.

Compounds of formula (I), pharmaceutically acceptable salts thereof and pharmaceutical compositions incorporating such may conveniently be administered by any of the routes conventionally used for drug administration, for instance, orally, topically, parenterally or by inhalation. The compounds of formula (I) may be administered in conventional dosage forms prepared by combining a compound of formula (I) with standard pharmaceutical carriers according to conventional procedures. The compounds of formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of formula (I) may be administered topically, that is by non-systemic administration. This includes the application of a compound of formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan esteror a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formua (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of formula (I), the daily oral dosage regimen will preferably be from about 0.1 to about 80 mg/kg of total body weight, preferably from about 0.2 to 30 mg/kg, more preferably from about 0.5 mg to 15 mg. The daily parenteral dosage regimen about 0.1 to about 80 mg/kg of total body weight, preferably from about 0.2 to about 30 mg/kg, and more preferably from about 0.5 mg to 15 mg/kg. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of formula (I) or a pharmaceutically acceptable salt thereof given per day for a defined number of days, can be ascertained by those skilled in the art using conventional course of treatment determination tests.

Biological Examples
LPS-induced TNFα Production in Mice and Rats

In order to evaluate in vivo inhibition of LPS-induced TNFα production in rodents, both mice and rats are injected with LPS.

Mouse Method

Male Balb/c mice from Charles River Laboratories are pretreated (30 minutes) with compound or vehicle. After the 30 min pretreat time, the mice are given LPS (lipopolysaccharide from *Esherichia coli* Serotype 055–85, Sigma Chemical Co., St Louis, Mo.) 25 ug/mouse in 25 ul phosphate buffered saline (pH 7.0) intraperitoneally. Two hours later the mice are killed by $CO_2$ inhalation and blood samples are collected by exsanguination into heparinized blood collection tubes and stored on ice. The blood samples are centrifuged and the plasma collected and stored at −20° C. until assayed for TNFα by ELISA.

Rat Method

Male Lewis rats from Charles River Laboratories are pretreated at various times with compound or vehicle. After a determined pretreat time, the rats are given LPS (lipopolysaccharide from *Esherichia coli* Serotype 055–85, Sigma Chemical Co., St Louis, Mo.) 3.0 mg/kg intraperitoneally. The rats are killed by $CO_2$ inhalation and heparinized whole blood is collected from each rat by cardiac puncture 90 minutes after the LPS injection. The blood samples are centrifuged and the plasma collected for analysis by ELISA for TNFα levels.

ELISA Method

TNFα levels were measured using a sandwich ELISA, as described in Olivera et al., Circ. Shock, 37, 301–306, (1992), whose disclosure is incorporated by reference in its entirety herein, using a hamster monoclonal antimurine TNFα (Genzyme, Boston, Mass.) as the capture antibody and a polyclonal rabbit antimurine TNFa (Genzyme) as the second antibody. For detection, a peroxidase-conjugated goat anti-rabbit antibody (Pierce, Rockford, Ill.) was added, followed by a substrate for peroxidase (1 mg/ml orthophenylenediamine with 1% urea peroxide). TNFα levels in the plasma samples from each animal were calculated from a standard curve generated with recombinant murine TNFα (Genzyme).

Cytokine Specific Binding Protein Assay

A radiocompetitive binding assay was developed to provide a highly reproducible primary screen for structure-activity studies. This assay provides many advantages over the conventional bioassays which utilize freshly isolated human monocytes as a source of cytokines and ELISA assays to quantify them. Besides being a much more facile assay, the binding assay has been extensively validated to highly correlate with the results of the bioassay. A specific and reproducible cytokine inhibitor binding assay was developed using soluble cystosolic fraction from THP. 1 cells and a radiolabeled compound. Patent Application U.S. Ser. No. 08/123,175 Lee et al., filed September 1993, USSN; Lee et al., PCT 94/10529 filed Sep. 16, 1994 and Lee et al., Nature 300, n(72), 739–746 (December 1994) whose disclosures are incorporated by reference herein in its entirety describes the above noted method for screening drugs to identify compounds which interact with and bind to the cytokine specific binding protein (hereinafter CSBP). However, for purposes herein the binding protein may be in isolated form in solution, or in immobilized form, or may be genetically engineered to be expressed on the surface of recombinant host cells such as in phage display system or as fusion proteins. Alternatively, whole cells or cytosolic fractions comprising the CSBP may be employed in the screening protocol. Regardless of the form of the binding protein, a plurality of compounds are contacted with the binding protein under conditions sufficient to form a compound/binding protein complex and compound capable of forming, enhancing or interfering with said complexes are detected.

CSBP Kinase Assay

This assay measures the CSBP-catalyzed transfer of $^{32}p$ from $[a-^{32}P]ATP$ to threonine residue in an epidermal growth factor receptor (EGFR)-derived peptide (T669) with the following sequence: KRELVEPLTPSGEAPNQALLR (residues 661–681). (See Gallagher et al., "Regulation of Stress Induced Cytokine Production by Pyridinyl Imidazoles: Inhibition of CSPB Kinase", BioOrganic & Medicinal Chemistry, 1997, 5, 49–64).

Reactions were carried in round bottom 96 well plate (from Corning) in a 30 $\mu$l volume. Reactions contained (in final concentration): 25 mM Hepes, $pH_{7.5;}$ 8 mM $MgCl_2$; 0.117 mM ATP (the $Km_{[ATP]}$ of p38 (see Lee et al., Nature 300, n72 pg. 639–746 (December 1994)); 2.5 uCi of [γ-32P] ATP; 0.2 mM sodium orthovanadate; 1 mM DTT; 0.1% BSA; 10% glycerol; 0.67 mM T669 peptide; and 2–4 nM of yeast-expressed, activated and purified p38. Reactions were initiated by the addition of [gamma-32P]Mg/ATP, and incubated for 25 min at 37° C. Inhibitors (dissolved in DMSO) were incubated with the reaction mixture on ice for 30 minutes prior to adding the 32P-ATP. Final DMSO concentration was 0.16%. Reactions were terminated by adding 10 ul of 0.3 M phosphoric acid, and phosphorylated peptide was isolated from the reactions by capturing it on p81 phosphocellulose filters. Filters were washed with 75 mM phosphoric acids, and incorporated 32P was quantified using beta scintillation counter. Under these conditions, the specific activity of p38 was 400–450 pmol/pmol enzyme, and the activity was linear for up to 2 hr of incubation. The kinase activity values were obtained after subtracting values generated in the absence of substrate which were 10–15% of total values.

Representative final compounds of Formula (I), Examples 1 to 4 have demonstrated positive inhibitory activity of an $IC_{50}$ of <50 uM in this binding assay.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound of the formula:

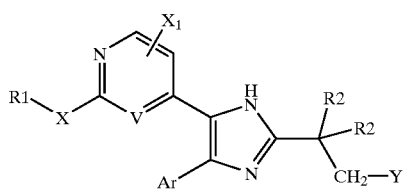

(I)

wherein

X is oxygen, carbon, sulfur, or nitrogen, or the moiety X—$R_1$ is hydrogen;

V is CH;

$R_1$ is hydrogen, $C_{1-6}$alkyl, aryl, aryl$C_{1-6}$alkyl, pyrrolidine, piperidine, piperazine, morpholine, imidazolidine, pyrazolidine, pyrrolidine $C_{1-6}$alkyl, piperidine $C_{1-6}$alkyl, piperazine $C_{1-6}$alkyl, morpholine $C_{1-6}$alkyl, imidazolidine $C_{1-6}$alkyl, pyrazolidine $C_{1-6}$alkyl, pyrrole, quinoline, isoquinoline, pyridine, pyrimidine, oxazole, thiazole, thiadiazole, triazole, imidazole, or benzimidazole, pyrrole $C_{1-6}$alkyl, quinoline $C_{1-6}$alkyl, isoquinoline $C_{1-6}$alkyl, pyridine $C_{1-6}$alkyl, pyrimidine $C_{1-6}$alkyl, oxazole $C_{1-6}$alkyl, thiazole $C_{1-6}$alkyl, thiadiazole $C_{1-6}$alkyl, triazole $C_{1-6}$alkyl, imidazole $C_{1-6}$alkyl, or benzimidazole $C_{1-6}$alkyl;

wherein each of these moieties may be optionally substituted;

$X_1$ is hydrogen, $XR_1$, optionally substituted $C_{1-4}$ alkyl, halogen, hydroxy, optionally substituted $C_{1-4}$ alkoxy, optionally substituted $C_{1-4}$ alkylthio, optionally substituted $C_{1-4}$ alkylsulfinyl, $CH_2OR_{12}$, amino, mono and di-$C_{1-6}$ alkyl substituted amino, $N(R_{10})C(O)R_b$, $N(R_{10})S(O)_2R_d$, or an N-heterocyclyl ring which ring has from 5 to 7 members and optionally contains an additional heteroatom selected from oxygen, sulfur or $NR_{15}$;

$R_b$ is hydrogen, $C_{1-6}$ alkyl, $C_{3-7}$ cycloalkyl, aryl, aryl$C_{1-4}$ alkyl, pyrrolidine, piperidine, piperazine, morpholine, imidazolidine, pyrazolidine, pyrrolidine $C_{1-4}$alkyl, piperidine $C_{1-4}$alkyl, piperazine $C_{1-4}$alkyl, morpholine $C_{1-4}$alkyl, imidazolidine $C_{1-4}$alkyl, pyrazolidine $C_{1-4}$alkyl, pyrrole, quinoline, isoquinoline, pyridine, pyrimidine, oxazole, thiazole, thiadiazole, triazole, imidazole, or benzimidazole, pyrrole $C_{1-4}$alkyl, quinoline $C_{1-4}$alkyl, isoquinoline $C_{1-4}$alkyl, pyridine $C_{1-4}$alkyl, pyrimidine $C_{1-4}$alkyl, oxazole $C_{1-64}$alkyl, thiazole $C_{1-4}$alkyl, thiadiazole $C_{1-4}$alkyl, triazole $C_{1-4}$alkyl, imidazole $C_{1-4}$alkyl, or benzimidazole $C_{1-4}$alkyl;

$R_d$ is $C_{1-6}$ alkyl, $C_{3-7}$ cycloalkyl, aryl, aryl$C_{1-4}$ alkyl, pyrrolidine, piperidine, piperazine, morpholine, imidazolidine, pyrazolidine, pyrrolidine $C_{1-4}$alkyl, piperidine $C_{1-4}$alkyl, piperazine $C_{1-4}$alkyl, morpholine $C_{1-4}$alkyl, imidazolidine $C_{1-4}$alkyl, pyrazolidine $C_{1-4}$alkyl, pyrrole, quinoline, isoquinoline, pyridine, pyrimidine, oxazole, thiazole, thiadiazole, triazole, imidazole, or benzimidazole, pyrrole $C_{1-4}$alkyl, quinoline $C_{1-4}$alkyl, isoquinoline $C_{1-4}$alkyl, pyridine $C_{1-4}$alkyl, pyrimidine $C_{1-4}$alkyl, oxazole $C_{1-64}$alkyl, thiazole $C_{1-4}$alkyl, thiadiazole $C_{1-4}$alkyl, triazole $C_{1-4}$alkyl, imidazole $C_{1-4}$alkyl, or benzimidazole $C_{1-4}$alkyl;

$R_2$ is independently an optionally substituted $C_{1-4}$ alkyl, and wherein the two $R_2$ moieties may together form a $C_{3-7}$ cycloalkyl or $C_{5-7}$ cycloalkenyl ring which ring may be optionally substituted;

Y is a $C_{2-4}$ alkenyl, hydroxy substituted $C_{1-4}$alkyl, pyrrolidine, piperidine, piperazine, morpholine, imidazolidine, pyrazolidine or $N(R_{10})C(Z)R_3$;

$R_3$ is $C_{1-6}$alkyl, aryl, aryl$C_{1-6}$alkyl, pyrrolidine, piperidine, piperazine, morpholine, imidazolidine, pyrazolidine, pyrolidine $C_{1-6}$alkyl, piperidine $C_{1-6}$alkyl, piperazine $C_{1-6}$alkyl, morpholine $C_{1-6}$alkyl, imidazolidine $C_{1-6}$alkyl, pyrazolidine $C_{1-6}$alkyl, pyrrole, quinoline, isoquinoline, pyridine, pyrimidine, oxazole, thiazole, thiadiazole, triazole, imidazole, or benzimidazole, pyrrole $C_{1-6}$alkyl, quinoline $C_{1-6}$alkyl, isoquinoline $C_{1-6}$alkyl, pyridine $C_{1-6}$alkyl, pyrimidine $C_{1-6}$alkyl, oxazole $C_{1-6}$alkyl, thiazole $C_{1-6}$alkyl, thiadiazole $C_{1-6}$alkyl, triazole $C_{1-6}$alkyl, imidazole $C_{1-6}$alkyl, or benzimidazole $C_{1-6}$alkyl;

wherein each of these moieties may be optionally substituted;

Ar is an aryl ring which ring may be optionally substituted;

$R_{10}$ is hydrogen or $C_{1-4}$alkyl;

$R_{12}$ is hydrogen, $C(Z)R_{13}$ or optionally substituted $C_{1-4}$ alkyl, optionally substituted aryl, optionally substituted aryl$C_{1-4}$ alkyl, or $S(O)_2R_{25}$;

Z is oxygen or sulfur;

$R_{13}$ is hydrogen, $C_{1-10}$ alkyl, $C_{3-7}$ cycloalkyl, pyrrolidine, piperidine, piperazine, morpholine, imidazolidine, pyrazolidine, pyrrolidine $C_{1-10}$ alkyl, piperidine $C_{1-10}$ alkyl, piperazine $C_{1-10}$alkyl, morpholine $C_{1-10}$alkyl, imidazolidine $C_{1-10}$alkyl, pyrazolidine $C_{1-10}$alkyl, pyrrole, quinoline, isoquinoline, pyridine, pyrimidine, oxazole, thiazole, thiadiazole, triazole, imidazole, or benzimidazole, pyrrole $C_{1-10}$alkyl, quinoline $C_{1-10}$alkyl, isoquinoline $C_{1-10}$alkyl, pyridine $C_{1-10}$alkyl, pyrimidine $C_{1-10}$alkyl, oxazole $C_{1-10}$alkyl, thiazole $C_{1-10}$alkyl, thiadiazole $C_{1-10}$alkyl, triazole $C_{1-10}$alkyl, imidazole $C_{1-10}$alkyl, or benzimidazole $C_{1-10}$alkyl;

wherein all of these moieties may be optionally substituted;

$R_{15}$ is hydrogen, cyano, $C_{1-4}$ alkyl, $C_{3-7}$ cycloalkyl or aryl;

$R_{25}$ is $C_{1-10}$ alkyl, $C_{3-7}$ cycloalkyl, heterocyclyl, aryl, arylalkyl, pyrrolidine, piperidine, piperazine, morpholine, imidazolidine, pyrazolidine, pyrrolidine $C_{1-10}$ alkyl, piperidine $C_{1-10}$ alkyl, piperazine $C_{1-10}$alkyl, morpholine $C_{1-10}$alkyl, imidazolidine $C_{1-10}$alkyl, pyrazolidine $C_{1-10}$alkyl, pyrrole, quinoline, isoquinoline, pyridine, pyrimidine, oxazole, thiazole, thiadiazole, triazole, imidazole, or benzimidazole, pyrrole $C_{1-10}$alkyl, quinoline $C_{1-10}$alkyl, isoquinoline $C_{1-10}$alkyl, pyridine $C_{1-10}$alkyl, pyrimidine $C_{1-10}$alkyl, oxazole $C_{1-10}$alkyl, thiazole $C_{1-10}$alkyl, thiadiazole $C_{1-10}$alkyl, triazole $C_{1-10}$alkyl, imidazole $C_{1-10}$alkyl, or benzimidazole $C_{1-10}$alkyl; or pharmaceutically acceptable salt thereof.

2. The compound according to claim 1 wherein X is oxygen.

3. The compound according to claim 1 wherein X is nitrogen.

4. The compound according to claim 1 wherein X is carbon.

5. The compound according to claim 1 wherein X—$R_1$ is hydrogen.

6. The compound according to claim 2 wherein $R_1$ is $C_{1-6}$alkyl, aryl, or aryl$C_{1-6}$alkyl.

7. The compound according to claim 3 wherein $R_1$ is hydrogen, $C_{1-6}$alkyl, aryl, or aryl$C_{1-6}$alkyl.

8. The compound according to claim 4 wherein $R_1$ is hydrogen, $C_{1-6}$alkyl, aryl, or aryl$C_{1-6}$alkyl.

9. The compound according to claim 1 wherein Ar is an optionally substituted phenyl.

10. The compound according to claim 9 wherein the phenyl is substituted by one or more times by halogen, $S(O)_mR_8$, $OR_8$ or $(CR_{10}R_{20})_mNR_{10}R_{20}$.

11. The compound according to claim 1 wherein Y is a pyrrolidine, piperidine, piperazine, morpholine, imidazolidine, or pyrazolidine.

12. The compound according to claim 1 wherein Y is $N(R_{10})C(Z)R_3$.

13. The compound according to claim 1 which is:
2-(1,1-Dimethyl-3-butenyl)-4-(4-fluorophenyl)-5-(4-pyridinyl)imidazole;
2-[2-(N-Benzoyl-N-methylamino)-(1,1-dimethyl)ethyl]-4-(4-fluorophenyl)-5-(4-pyridinyl)imidazole; or
(+/−)-2-[(3,4-Dihydroxy)-1,1-dimethylbutyl]-4-(4-fluorophenyl)-5-(4-pyridinyl)imidazole; or
a pharmaceutically acceptable salt thereof.

14. The compound according to claim 1 wherein $X_1$ is hydrogen.

15. The compound according to claim 1 wherein $R_2$ is independently an optionally substituted $C_{1-4}$ alkyl.

16. The compound according to claim 1 wherein Z is oxygen.

17. The compound according to claim 9 wherein the aryl substituent is halogen, $OR_8$, amino, $NR_{10}C(Z)R_8$, or $NR_{10}S(O)mR_{11}$.

18. A compound of the formula:

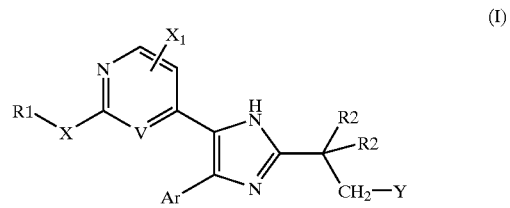

wherein
X is oxygen, carbon, sulfur, or nitrogen, or the moiety X—$R_1$ is hydrogen;
V is CH;
$R_1$ is hydrogen, $C_{1-6}$alkyl, aryl, aryl$C_{1-6}$alkyl, pyrrolidine, piperidine, piperazine, morpholine, imidazolidine, pyrazolidine, pyrrolidine $C_{1-6}$alkyl, piperidine $C_{1-6}$alkyl, piperazine $C_{1-6}$alkyl, morpholine $C_{1-6}$alkyl, imidazolidine $C_{1-6}$alkyl, pyrazolidine $C_{1-6}$alkyl, pyrrole, quinoline, isoquinoline, pyridine, pyrimidine, oxazole, thiazole, thiadiazole, triazole, imidazole, or benzimidazole, pyrrole $C_{1-6}$alkyl, quinoline $C_{1-6}$alkyl, isoquinoline $C_{1-6}$alkyl, pyridine $C_{1-6}$alkyl, pyrimidine $C_{1-6}$alkyl, oxazole $C_{1-6}$alkyl, thiazole $C_{1-6}$alkyl, thiadiazole $C_{1-6}$alkyl, triazole $C_{1-6}$alkyl, imidazole $C_{1-6}$alkyl, or benzimidazole $C_{1-6}$alkyl;

wherein each of these moieties may be optionally substituted;

$X_1$ is hydrogen, $XR_1$, optionally substituted $C_{1-4}$ alkyl, halogen, hydroxy, optionally substituted $C_{1-4}$ alkoxy, optionally substituted $C_{1-4}$ alkylthio, optionally substituted $C_{1-4}$ alkylsulfinyl, $CH_2OR_{12}$, amino, mono and di-$C_{1-6}$ alkyl substituted amino, $N(R_{10})C(O)R_b$, $N(R_{10})S(O)_2R_d$, or an N-heterocyclyl ring which ring has from 5 to 7 members and optionally contains an additional heteroatom selected from oxygen, sulfur or $NR_{15}$;

$R_b$ is hydrogen, $C_{1-6}$ alkyl, $C_{3-7}$ cycloalkyl, aryl, aryl$C_{1-4}$ alkyl, pyrrolidine, piperidine, piperazine, morpholine, imidazolidine, pyrazolidine, pyrrolidine $C_{1-4}$alkyl, piperidine $C_{1-4}$alkyl, piperazine $C_{1-4}$alkyl, morpholine $C_{1-4}$alkyl, imidazolidine $C_{1-4}$alkyl, pyrazolidine $C_{1-4}$alkyl, pyrrole, quinoline, isoquinoline, pyridine, pyrimidine, oxazole, thiazole, thiadiazole, triazole, imidazole, or benzimidazole, pyrrole $C_{1-4}$alkyl, quinoline $C_{1-4}$alkyl, isoquinoline $C_{1-4}$alkyl, pyridine $C_{1-4}$alkyl, pyrimidine $C_{1-4}$alkyl, oxazole $C_{1-64}$alkyl, thiazole $C_{1-4}$alkyl, thiadiazole $C_{1-4}$alkyl, triazole $C_{1-4}$alkyl, imidazole $C_{1-4}$alkyl, or benzimidazole $C_{1-4}$alkyl;

$R_d$ is $C_{1-6}$ alkyl, $C_{3-7}$ cycloalkyl, aryl, aryl$C_{1-4}$ alkyl, pyrrolidine, piperidine, piperazine, morpholine, imidazolidine, pyrazolidine, pyrrolidine $C_{1-4}$alkyl, piperidine $C_{1-4}$alkyl, piperazine $C_{1-4}$alkyl, morpholine $C_{1-4}$alkyl, imidazolidine $C_{1-4}$alkyl, pyrazolidine $C_{1-4}$alkyl, pyrrole, quinoline, isoquinoline, pyridine, pyrimidine, oxazole, thiazole, thiadiazole, triazole, imidazole, or benzimidazole, pyrrole $C_{1-4}$alkyl, quinoline $C_{1-4}$alkyl, isoquinoline $C_{1-4}$alkyl, pyridine $C_{1-4}$alkyl, pyrimidine $C_{1-4}$alkyl, oxazole $C_{1-64}$alkyl, thiazole $C_{1-4}$alkyl, thiadiazole $C_{1-4}$alkyl, triazole $C_{1-4}$alkyl, imidazole $C_{1-4}$alkyl, or benzimidazole $C_{1-4}$alkyl;

$R_2$ is independently an optionally substituted $C_{1-4}$ alkyl, and wherein the two $R_2$ moieties may together form a $C_{3-7}$ cycloalkyl or $C_{5-7}$ cycloalkenyl ring which ring may be optionally substituted;

Y is a $C_{2-4}$ alkenyl, hydroxy substituted $C_{1-4}$ alkyl, pyrrolidine, piperidine, piperazine, morpholine, imidazolidine, pyrazolidine, or $N(R_{10})C(Z)R_3$;

$R_3$ is $C_{1-6}$alkyl, aryl, aryl$C_{1-6}$alkyl, pyrrolidine, piperidine, piperazine, morpholine, imidazolidine, pyrazolidine, pyrrolidine $C_{1-6}$alkyl, piperidine $C_{1-6}$alkyl, piperazine $C_{1-6}$alkyl, morpholine $C_{1-6}$alkyl, imidazolidine $C_{1-6}$alkyl, pyrazolidine $C_{1-6}$alkyl, pyrrole, quinoline, isoquinoline, pyridine, pyrimidine, oxazole, thiazole, thiadiazole, triazole, imidazole, or benzimidazole, pyrrole $C_{1-6}$alkyl, quinoline $C_{1-6}$alkyl, isoquinoline $C_{1-6}$alkyl, pyridine $C_{1-6}$alkyl, pyrimidine $C_{1-6}$alkyl, oxazole $C_{1-6}$alkyl, thiazole $C_{1-6}$alkyl, thiadiazole $C_{1-6}$alkyl, triazole $C_{1-6}$alkyl, imidazole $C_{1-6}$alkyl, or benzimidazole $C_{1-6}$alkyl;

wherein each of these moieties may be optionally substituted;

Ar is an optionally substituted naphthyl;

$R_{10}$ is hydrogen or $C_{1-4}$ alkyl;

$R_{12}$ is hydrogen, $C(Z)R_{13}$ or optionally substituted $C_{1-4}$ alkyl, optionally substituted aryl, optionally substituted aryl$C_{1-4}$ alkyl, or $S(O)_2R_{25}$;

Z is oxygen or sulfur;

$R_{13}$ is hydrogen, $C_{1-10}$ alkyl, $C_{3-7}$ cycloalkyl, aryl, aryl$C_{1-10}$ alkyl, pyrrolidine, piperidine, piperazine, morpholine, imidazolidine, pyrazolidine, pyrrolidine $C_{1-10}$ alkyl, piperidine $C_{1-10}$ alkyl, piperazine $C_{1-10}$alkyl, morpholine $C_{1-10}$alkyl, imidazolidine $C_{1-10}$alkyl, pyrazolidine $C_{1-10}$alkyl, pyrrole, quinoline, isoquinoline, pyridine, pyrimidine, oxazole, thiazole, thiadiazole, triazole, imidazole, or benzimidazole, pyrrole $C_{1-10}$alkyl, quinoline $C_{1-10}$alkyl, isoquinoline $C_{1-10}$alkyl, pyridine $C_{1-10}$alkyl, pyrimidine $C_{1-10}$alkyl, oxazole $C_{1-10}$alkyl, thiazole $C_{1-10}$alkyl, thiadiazole $C_{1-10}$alkyl, triazole $C_{1-10}$alkyl, imidazole $C_{1-10}$alkyl, or benzimidazole $C_{1-10}$alkyl; wherein all of these moieties may be optionally substituted;

$R_{15}$ is hydrogen, cyano, $C_{1-4}$ alkyl, $C_{3-7}$ cycloalkyl or aryl;

$R_{25}$ is $C_{1-10}$ alkyl, $C_{3-7}$ cycloalkyl, heterocyclyl, aryl, arylalkyl, pyrrolidine, piperidine, piperazine, morpholine, imidazolidine, pyrazolidine, pyrrolidine $C_{1-10}$ alkyl, piperidine $C_{1-10}$ alkyl, piperazine $C_{1-10}$alkyl, morpholine $C_{1-10}$alkyl, imidazolidine $C_{1-10}$alkyl, pyrazolidine $C_{1-10}$alkyl, pyrrole, quinoline, isoquinoline, pyridine, pyrimidine, oxazole, thiazole, thiadiazole, triazole, imidazole, or benzimidazole, pyrrole $C_{1-10}$alkyl, quinoline $C_{1-10}$alkyl, isoquinoline $C_{1-10}$alkyl, pyridine $C_{1-10}$alkyl, pyrimidine $C_{1-10}$alkyl, oxazole $C_{1-10}$alkyl, thiazole $C_{1-10}$alkyl, thiadiazole $C_{1-10}$alkyl, triazole $C_{1-10}$alkyl, imidazole $C_{1-10}$alkyl, or benzimidazole $C_{1-10}$alkyl; or a pharmaceutically acceptable salt thereof.

19. The compound according to claim 18 wherein the Ar ring is optionally substituted one or more times by halogen, $S(O)_mR_8$, $OR_8$, $(CR_{10}R_{20})_mNR_{10}R_{20}$, $NR_{10}C(Z)R_8$, or $NR_{10}S(O)_mR_{11}$.

20. The compound according to claim 18 wherein the Ar is substituted one or more times by halogen, $SR_8$, $SOR_8$, $OR_8$, amino, $NR_{10}C(Z)R_8$, or $NR_{10}S(O)mR_{11}$.

21. The compound according to claim 18 wherein Y is $N(R_{10})C(Z)R_3$.

22. A pharmaceutical composition comprising a compound according to claim 1, and a pharmaceutically acceptable carrier or diluent.

23. A method of treating a CSBP/RK/p38 kinase mediated disease selected from rheumatoid arthritis, osteoarthritis, and gouty arthritis in a mammal in need thereof, comprising administering to said mammal an effective amount of a compound according to claim 1.

24. A pharmaceutical composition comprising a compound according to claim 18 and a pharmaceutically acceptable carrier or diluent.

25. A method of treating a CSBP/RK/p38 kinase mediated disease selected from rheumatoid arthritis, osteoarthritis, and gouty arthritis in a mammal in need thereof, comprising administering to said mammal an effective amount of a compound according to claim 18.

\* \* \* \* \*